(12) United States Patent
Ying et al.

(10) Patent No.: US 8,372,643 B2
(45) Date of Patent: Feb. 12, 2013

(54) METHOD FOR EXTRACELLULAR MATRIX MEDIATED DIFFERENTIATION AND PROLIFERATION OF STEM CELLS

(75) Inventors: Jackie Y. Ying, Singapore (SG); Andrew Chwee Aun Wan, Singapore (SG); Karthikeyan Narayanan, Singapore (SG); Karl M. Schumacher, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 12/746,512

(22) PCT Filed: Dec. 5, 2008

(86) PCT No.: PCT/SG2008/000467
§ 371 (c)(1),
(2), (4) Date: Jun. 4, 2010

(87) PCT Pub. No.: WO2009/072990
PCT Pub. Date: Jun. 11, 2009

(65) Prior Publication Data
US 2010/0285585 A1    Nov. 11, 2010

Related U.S. Application Data

(60) Provisional application No. 60/996,816, filed on Dec. 6, 2007.

(51) Int. Cl.
*C12N 5/00* (2006.01)
*C12N 5/02* (2006.01)
(52) U.S. Cl. .................... 435/377; 435/373; 435/375
(58) Field of Classification Search .................. None
See application file for complete search history.

(56) References Cited

U.S. PATENT DOCUMENTS

| | | | |
|---|---|---|---|
| 2002/0072117 A1 | 6/2002 | Xu et al. | |
| 2005/0124063 A1 | 6/2005 | Yang et al. | |
| 2005/0153444 A1 | 7/2005 | Mandalam et al. | |
| 2005/0214939 A1 | 9/2005 | Gold et al. | |
| 2007/0155009 A1 | 7/2007 | McClelland | |
| 2007/0280907 A1 | 12/2007 | Lue et al. | |

FOREIGN PATENT DOCUMENTS

| | | |
|---|---|---|
| EP | 1669441 | 6/2006 |
| WO | 93/17696 A1 | 9/1993 |
| WO | WO 99/20741 | 4/1999 |
| WO | WO 99/53021 | 10/1999 |
| WO | 01/51616 A1 | 7/2001 |
| WO | WO 2006/104901 | 10/2006 |
| WO | WO 2007/002086 | 1/2007 |
| WO | WO 2007/117472 | 10/2007 |

OTHER PUBLICATIONS

Stem Cells: Scientific Progress and Future Research Directions. Chapter 2, pp. 5-10. Department of Health and Human Services. Jun. 2001. http://www.nih.gov/news/stemcell/scireport.htm.*
Lin et al. (Jul. 2010) Fibronectin and laminin promote differentiation of human mesenchymal stem cells into insulin producing cells through activating Akt and ERK. Journal of Biomedical Science 17: 56.*
Ilic, D. Culture of human embryonic stem cells and the extracellular matrix microenvironment. Regenerative Medicine vol. 1(1), 95-101 (2006).
Sun, Y. et al. Differentiation of bone marrow-derived mesenchymal stem cells from diabetic patients into insulin-producing cells invitro. Chinese Medical Journal, vol. 120(9), 771-776 (2007).
Segev, H. et al. Differentiation of human embryonic stem cells into insulin-producing clusters. Stem Cells. 22(3):265-274 (2004).
Singec, I; Jandial, R; Crain, A; Nikkhah, G; Snyder, EY (2007) The leading edge of stem cell therapeutics. Annual Reviews in Medicine 58: 313-328.
Findikli, N; Candan, NZ; Kahraman, S (2006) Human embryonic stem cell culture: Current limitations and novel strategies. Reproductive Biomedicine Online 13: 581-590.
Wobus, AM; Boheler, KR (2005) Embryonic stem cells: Prospects for developmental biology and cell therapy. Physiological Reviews 85: 635-678.
Barry, FP; Murphy, JM (2004) Mesenchymal stem cells: Clinical applications and biological characterization. International Journal of Biochem. and Cell Biol. 36: 568-584.
Filipczyk, AA; et al. (2007) Regulation of cardiomyocyte differentiation of embryonic stem cells by extracellular signaling. Cell. and Mol Life Sciences 64: 704-718.
van Wijk, B; Moorman, AFM; van den Hoff, MJB (2007) Role of bone morphogenetic proteins in cardiac differentiation. Cardiovascular Research 74: 244-255.
Ye, P; D'Ercole, AJ (2006) Insulin-like growth factor actions during development of neural stem cells and progenitors in the central nervous system. J Neuroscience Research 83: 1-6.
Spagnoli, FM; Hemmati-Brivanlou, A (2006) Guiding embryonic stem cells towards differentiation: Lessons from molecular embryology. Current Opinion in Genetics and Development 16: 469-475.
Berry, MF; et al. (2006) Mesenchymal stem cell injection after myocardial infarction improves myocardial compliance. Am J Physiology Heart and Circulatory Physiology 290: H2196-H2203.
Murry, CE; Reinecke, H; Pabon, LM (2006) Regeneration gaps— Observations on stem cells and cardiac repair. J American College of Cardiology 47: 1777-1785.
Lange, C; et al. (2005) Administered mesenchymal stem cells enhance recovery from Ischemla/reperfusion-induced acute renal failure in rats. Kidney International 68: 1613-1617.

(Continued)

*Primary Examiner* — Anne-Marie Falk
(74) *Attorney, Agent, or Firm* — Klarquist Sparkman, LLP

(57) ABSTRACT

There is provided a method of culturing a stem cell on extracellular matrix extracted from support cells and in a stem cell culture medium comprising medium conditioned by the support cells.

10 Claims, 10 Drawing Sheets

OTHER PUBLICATIONS

Kajstura, J; et al. (2005) Bone marrow cells differentiate in cardiac cell lineages after infarction independently of cell fusion. Circulation Research 96: 127-137.

Chen, SL; et al. (2004) Effect on left ventricular function of intracoronary transplantation of autologous bone marrow mesenchymal stem cell in patients with acute myocardial infarction. Am J Cardiology 94: 92-95.

Nakano, K; et al. (2001) Differentiation of transplanted bone marrow cells in the adult mouse brain. Transplantation 71: 1735-1740.

Kopen, GC; Prockop, DJ; Phinney, DG (1999) Marrow stromal cells migrate throughout forebrain and cerebellum, and they differentiate into astrocytes after injection into neonatal mouse brains. PNAS 96: 10711-10716.

Pluchino, S; et al. (2003) Injection of adult neurospheres induces recovery in a chronic model of multiple sclerosis. Nature 422: 688-694.

Little, M.H. Regrow or repair: Potential regenerative therapies for the kidney. J Am Soc Nephrol 17, 2390-2401 (2006).

Wang, G. et al. Noggin and bFGF cooperate to maintain the pluripotency of human embryonic stem cells in the absence of feeder layers. Biochem Biophys Res Commun 330, 934-942 (2005).

Pittenger, M. et al. Multilineage potential of adult human mesenchymal stem cells. Science. Apr. 2, 1999;284(5411)143-7.

Chen, L. Jiang, X. and Yang, L. Differentiation of rat marrow mesenchymal stem cells into pancreatic islet beta-cells. World J Gastroenterol. Oct. 15, 2004;10(20):3016-20.

Flaim CJ, Chien S, Bhatia SN. An extracellular matrix microarray for probing cellular differentiation. Nat Methods. Feb. 2005;2(2):119-25.

Amit, M and Itskovitz-Eldor, J. Feeder-free culture of human embryonic stem cells. Methods Enzymol. 2006;420:37-49.

Chase L. and Firpo, M. Development of serum-free culture systems for human embryonic stem cells. Curr Opin Chem Biol. Aug. 2007;11(4):367-72.

Ellerström C. et al. Derivation of a xeno-free human embryonic stem cell line. Stem Cells. Oct. 2006;24(10):2170-6.

Suzuki, A. et al. Role for growth factors and extracellular matrix in controlling differentiation of prospectively isolated hepatic stem cells. Development. Jun. 2003;130(11):2513-24.

Haylock D. and Nilsson, S. Stem cell regulation by the hematopoietic stem cell niche. Cell Cycle. Oct. 2005;4(10):1353-5.

Kihara, T. et al. Exogenous type I collagen facilitates osteogenic differentiation and acts as a substrate for mineralization of rat marrow mesenchymal stem cells in vitro. Biochem Biophys Res Commun. Mar. 24, 2006;341 (4):1029-35.

Chen, S. et al. Cell-cell and cell-extracellular matrix interactions regulate embryonic stem cell differentiation. Stem Cells. Mar. 2007;25(3):553-61.

Xu, C. et al. Feeder-free growth of undifferentiated human embryonic stem cells. Nat Biotechnol. Oct. 2001;19(10):971-4.

Naugle, J. et al. Type VI collagen induces cardiac myofibroblast differentiation: implications for postinfarction remodeling. Am J Physiol Heart Circ Physiol. Jan. 2006;290(1):H323-30.

Ludwig, T. et al. Derivation of human embryonic stem cells in defined conditions. Nat Biotechnol. Feb. 2006;24(2):185-7.

Derda, R. et al. Defined substrates for human embryonic stem cell growth identified from surface arrays. ACS Chem Biol. May 22, 2007;2(5):347-55.

Rajala, K. et al., Testing of nine different xeno-free culture media for human embryonic stem cell cultures. Hum Reprod. May 2007;22(5):1231-8.

Stojkovic, P. et al., Human-serum matrix supports undifferentiated growth of human embryonic stem cells. Stem Cells. Aug. 2005;23(7):895-902.

Humes, H.D. et al. Initial clinical results of the bioartificial kidney containing human cells in ICU patients with acute renal failure. Kidney Int 66, 1578-1588 (2004).

Tiranathanagul, K., Brodie, J. & Humes, H.D. Bioartificial kidney in the treatment of acute renal failure associated with sepsis. Nephrology (Carlton) 11, 285-291 (2006).

D'Amour, K. et al. Production of pancreatic hormone-expressing endocrine cells from human embryonic stem cells. Nat Biotechnol. Nov. 2006;24(11):1392-401.

Meyer, C. et al. Improved glucose counterregulation and autonomic symptoms after intraportal islet transplants alone in patients with long-standing type I diabetes mellitus. Transplantation. Jul. 27, 1998;66 (2):233-40.

Juang, J. et al. Outcome of subcutaneous islet transplantation improved by polymer device. Transplantation.Jun. 15, 1996;61.

P. Vaca, et al. Induction of differentiation of embryonic stem cells into insulin-secreting cells by fetal soluble factors. Stem Cells 2006, 24, 258-265.

J. Kramer, et al, Cells differentiated from mouse embryonic stem cells via embryoid bodies express renal marker molecules. Differentiation 2006, 74, 91-104.

S. Golcoa, et al. Sodium butyrate activates genes of early pancreatic development in embryonic stem cells. Cloning and Stem Cells 2006, 8, 140-149.

F. Lin, et al. Hematopoletic stem cells contribute to the regeneration of renal tubules after renal ischemia-reperfusion injury in mice. J. Am. Soc. Nephrol. 2003, 14, 1188-1199.

Lumelsky, N. et al. Differentiation of Embryonic Stem Cells to Insulin-Secreting Structures Similar to Pancreatic Islets. Science 2001, vol. 292, 1389-1394.

Klimanskaya, I. et al. Human embryonic stem cells derived without feeder cells. The Lancet 2005, vol. 365, 1636-1641.

International Search Report and Written Opinion for SG2008/000467 mailed Mar. 13, 2009.

International Preliminary Report on Patentability for SG2008/000467 mailed Nov. 9, 2009.

Schumacher, K.M. et al., "Controlled formation of biological tubule systems in extracellular matrix gens in vitro", Kidney International, 2008, pp. 1187-1192, vol. 73.

Extended European Search Report issued in corresponding EP Application No. 08856713.6 (dated Sep. 9, 2011).

Examination Report issued in corresponding EP Application No. 08856713.6 (dated Jul. 17, 2012).

\* cited by examiner

METHOD FOR EXTRACELLULAR MATRIX MEDIATED DIFFERENTIATION AND PROLIFERATION OF STEM CELLS

CROSS-REFERENCE TO RELATED APPLICATION

This application claims benefit of, and priority from, U.S. provisional patent applications No. 60/996,816, filed on Dec. 6, 2007, the contents of which are fully incorporated herein by reference.

FIELD OF THE INVENTION

The present invention relates to a method for culturing cells that can mediate differentiation and undifferentiated proliferation of stem cells.

BACKGROUND OF THE INVENTION

A major obstacle for various approaches in regenerative medicine aimed at replacing lost organ functions is the shortage of available cell sources. The availability of such approaches is often limited by the shortage of donor tissue. Stem cells, including embryonic or bone marrow derived mesenchymal stem cells, are a potential cell source for regenerative medicine (1-4). Human embryonic stem (hES) cells are capable of indefinite self-renewal and are pluripotent; that is, these cells are able to differentiate into practically every type of cell found in the organism from which they are derived (17, 18). Human mesenchymal stem (hMS) cells are multipotent and can differentiate into various cell lineages of mesenchymal tissues including, bone, cartilage, fat, tendon, muscle, adipocytes, chondrocytes, and osteocytes (19, 20). hES and hMS cells accordingly have tremendous potential to provide different cell types for use in a variety of medical and research purposes.

Techniques for in vitro differentiation of stem cells into particular cell lineages using specific proteins or chemical molecules have been well-studied. However, achieving a large population of differentiated functional cells remains a challenge.

To date, differentiation of stem cells in vitro has generally been limited to reliance on non-directed cell differentiation or inefficient methods for inducing differentiation that require the addition of various growth factors and supplements to the cell culture and that tend to produce a low percentage of desired differentiated cells (21, 40).

Similarly, achieving in vitro undifferentiated proliferation of hES cells suitable for clinical applications has been challenging. Traditional culture methods for proliferating human stem cells require the use of mouse embryonic fibroblasts (MEFs) as a feeder layer, which could result in cross-contamination of the human stem cell population with animal components (22). Contamination of stem cells or their differentiated derivatives with animal components increases the likelihood of immune rejection during regenerative therapies (23, 24).

SUMMARY OF THE INVENTION

The present invention provides a method of directed in vitro differentiation of stem cells. The method involves culturing stem cells in conditioned medium and on an extracellular matrix (ECM) extracted from cells to provide conditions that induce directed differentiation into cells functionally comparable to the cells from which the ECM was extracted.

In addition, the method of the present invention provides undifferentiated proliferation of stem cell in vitro. Using the method of the present invention, hES cells cultured, for example, on the ECM extracted from MEFs can be proliferated without differentiation.

Thus the present methods have the potential to provide a much needed cell source for regenerative medicine. The present methods may provide a high yield of differentiated cells of a desired cell type at a low cost, and in one embodiment also provide in vitro hES cell cultures that are free of cross contamination with MEFs. Such cultures are thus less likely to result in immune rejection when used in regenerative therapies.

In one aspect, there is provided a method comprising culturing a stem cell on extracellular matrix extracted from support cells and in a stem cell culture medium comprising medium conditioned by the support cells.

In one embodiment, the stem cell culture medium is free from the support cells.

In one embodiment, the support cells are differentiated. The support cells may be for example proximal tubule cells, pancreatic insulin-secreting cells, osteoblasts, neuronal cells, glial cells, hepatocytes, myoblasts or human proximal tubule cells.

In another embodiment the support cells provide conditioned medium and extracellular matrix that maintain the stem cell in an undifferentiated state and the culturing comprises proliferation of the stem cell without differentiation. The support cells may be for example mouse embryonic fibroblasts.

In different embodiments of the present method, the stem cell may be for example an embryonic stem cell, a mesenchymal stem cell, a human embryonic stem cell or a human mesenchymal stem cell.

In one embodiment, the stem cell is cultured in a tissue culture plate or culture flask.

In another embodiment, the support cells are differentiated and the stem cell is cultured in a bioartificial device. For example, the bioartificial device may be a bioartificial tubule assist device and the support cells may be human proximal tubule cells.

In one embodiment the stem cell culture medium comprises about 45% (v/v) to about 55% (v/v) medium conditioned by the support cells.

In another aspect, there is provided a population of cells differentiated from a population of stem cells on extracellular matrix extracted from support cells and in a stem cell culture medium comprising medium conditioned by the support cells, wherein about 30% or more of the cells are differentiated.

In one embodiment, the population of cells is prepared according to the methods of stem cell culturing described herein wherein the support cells are differentiated.

For example in one embodiment, the population of stems cells is a population of human mesenchymal stem cells and the support cells are pancreatic beta cells, wherein about 30% or more of the cells express insulin c-peptide.

In another embodiment, the population of stems cells is a population of human embryonic stem cells and the support cells are pancreatic beta cells, wherein about 30% or more of the cells express insulin c-peptide.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

Figure 1:
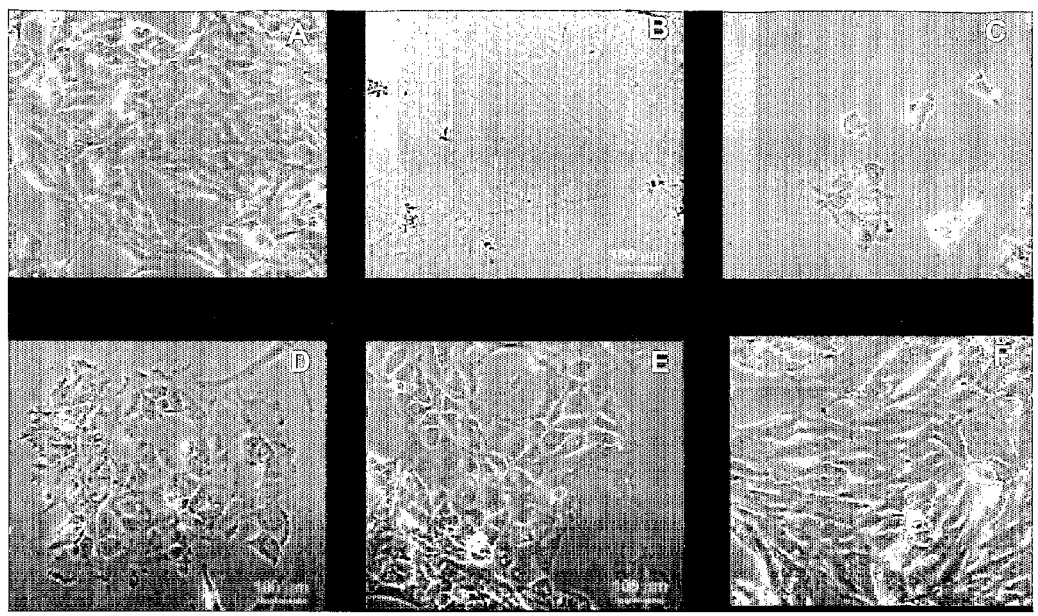
FIG. 1. Differentiation of hES cells into proximal tubule cells. Light microscopy images of (A) Human proximal tubule cells (HPTCs) cultured on fibronectin coated culture dishes, (B) ECM from HPTC culture, and differentiation of hESCs on HPTC ECM into proximal tubule cells after (C) 18 h, (D) 3 days, (E) 5 days and (F) 12 days. (F) The differentiated hESCs were subcultured in tissue culture treated dishes without any protein coating.

The methods described herein relate, in part, to the discovery that stem cells can be grown in the absence of feeder cells, using a specific extracted extracellular matrix. The extracted ECM, when used in combination with medium conditioned by the same cell type from which the ECM is extracted, provides support and growth factors to direct the proliferation, and optionally the differentiation, of the stem cells in culture. The inventors have discovered that using ECM extracted from MEFs allows for undifferentiated proliferation of stem cells, while the use of an ECM extracted from a differentiated cell population results in directed differentiation of the cultured stem cells.

Proliferation and differentiation of stem cells are regulated by the cellular microenvironment (21, 25, 26). Extracellular regulators include soluble factors such as growth factors, insoluble factors such as extracellular matrix (ECM) molecules and cell-cell interactions and physical stimuli such as shear stress (21, 27). Together these various factors form a complex niche of signals and interactions that regulate the fate and function of a stem cell. During embryogenesis, the development of specific tissue types from stem cells is highly complicated and tightly controlled by various transcription factors, signalling molecules and the presence of particular ECM molecules at particular stages of development (5-8, 28). Similarly, during tissue repair in adults, stem cells, recruited to the damaged sites by various chemokines and their receptors, are induced to undergo differentiation under the influence of the micro-environment of the specific tissue. The ECM provides the mechanical stability, growth factors and signalling molecules required for the differentiation of stem cells.

Although in the past, studies have focused on the role of growth factors in the regulation of stem cells, there is an increasing recognition of the critical role the ECM plays in stem cell regulation (21). Cellular interactions with the ECM can induce cell signalling, modulate cellular response to other signals and influence binding of the cell to other factors (21). Studies have demonstrated a critical role for the ECM in regulating stem cell differentiation and proliferation during embryogenesis (28) as well as in the differentiation of mesenchymal stem cells (27). Scientists have achieved on-site differentiation by injecting stem cells directly into damaged tissue (31, 32). For example, differentiation of stem cells into cardiomyoblasts and neurons has been observed upon injection into infarcted myocardial tissue and damaged brain tissue respectively (9-16). These studies indicate that the microenvironment plays a role in stem cell differentiation.

Stem cells require adhesion to an ECM for survival and growth (29). Traditional in vitro cell culture conditions for stem cells involve culturing the cells on MATRIGEL™ Matrix (BD Biosciences, Germany), a solubilized basement membrane secreted by mouse sarcoma cells that contains a combination of laminin, collagen IV, heparin sulphate proteoglycans, enactin and nidogen 1. While MATRIGEL™ sustains undifferentiated growth of stem cells, attempts have been made to define better matrices for stem cell proliferation and differentiation (23).

To date, differentiation methods have been limited to the use of purified or recombinant ECM molecules. Recombinant ECM molecules by nature differ from the ECM molecules found in the tissue; on the other hand, purified human matrix components are expensive (36, 34). Further, mixtures of purified ECM molecules will not provide the same diversity of signals and interactions provided by the whole complement of ECM secreted by cells to modify cell response and activate protein expression. A suspension compiled from various isolated ECM components will not provide the same combination of ECM molecules as that naturally secreted by the cell, or the full range of biological effects they provide.

Human sera, which contains ECM molecules including fibronectin, vitronectin and hyaluronic acid, has been used to sustain undifferentiated proliferation of hES cells in vitro (37). However, human sera does not provide ECM molecules in the same tissue-specific combinations that are found in the ECM of particular cells, and thus the same tissue-specific cell signals and interactions are also not provided. In addition, access to human sera is limited by the availability of blood donation and sera must be carefully tested for the presence of blood-borne pathogens such as hepatitis B, hepatitis C and the human immunodeficiency virus (37).

The present methods are based on the findings that culturing stem cells on an ECM extracted from cells has the potential to induce the differentiation or mediate the undifferentiated proliferation of the stem cells, depending on the type of cell from which the ECM is extracted.

The present methods provide a method of culturing a stem cell, the method comprising culturing a stem cell on ECM extracted from a culture of cells of a selected cell type (hereinafter "support cells") and in a stem cell culture medium containing medium conditioned by a culture of the support cells. The stem cells may be cultured in the absence of the support cells. The support cells of a selected cell type are grown in medium under conditions sufficient to allow for cell growth, in order to provide conditioned medium for the stem cell culture. The support cells themselves are used as a source of ECM, which is extracted from a culture of the support cells and then used as a substrate for culturing the stem cells. Thus, there is no need to include cells in the culture conditions except for the stem cells themselves.

Using the present methods, undifferentiated proliferation of stem cells is thus possible in the absence of feeder cells, which are typically required in known methods of culturing undifferentiated stem cells. In known methods of undifferentiated proliferation of stem cells, the stem cells are adhered on top of a layer of feeder cells, such as MEFs, and receive signals from the feeder cells that facilitate undifferentiated proliferation. Without being limited to any particular theory, it appears that in contrast, in the present method, the stem cells adhere onto the ECM extracted from support cells and receive signals from the ECM necessary for undifferentiated proliferation.

As used herein, the term "cell", including when used in the context of support cell or stem cell, is intended to refer to a single cell as well as a plurality or population of cells, where context allows. Similarly, the term "cells" is also intended to refer to a single cell, where context allows. The cell may be a cell grown in batch culture or in tissue culture plates.

The support cells are any cells that secrete ECM and can be cultured in medium to provide a cell culture from which an ECM can be extracted, and on which ECM the stems cell are to be cultured to resemble the support cells upon differentiation or to maintain an undifferentiated state. The support cell may be from the same organism as the stem cell to be cultured or may be from a different organism.

By selecting the specific cell type for the support cells, the growth of the stem cell in culture can be influenced. Thus, depending on the type of support cells used, the present methods of culturing a stem cell can be used to induce differentiation of the stem cell or to proliferate the stem cell.

If the stem cell to be cultured is to be differentiated, the support cell chosen is a differentiated cell of an appropriate lineage or cell type that will provide conditioned medium and ECM, and into which cell type the stem cell is to be differentiated. That is, by selecting a particular differentiated cell type to condition the medium and provide the ECM, the stem cell can be directed to differentiate to phenotypically and functionally resemble, or be phenotypically and functionally comparable to, the support cells used. "Phenotypically and functionally" resemble or be comparable to as used herein means that the differentiated cell has become the same cell type as the support cell, or that the differentiated cell resembles the support cell in that the differentiated cell has the same phenotypic markers that identify the support cell and has the same biological function as the support cell (excepting any genetic modification of the stem cell, species differences if the stem cell and support cell are from different organisms or limitations due to the level of commitment of the stem cell).

For example, the support cell may be a proximal tubule cell, a pancreatic insulin-secreting cell, a bone cell including an osteoblast, a brain cell including a neuronal cell or a glial cell, a hepatocyte, a myoblast, a smooth muscle cell, an endothelial cell, a cardiomyocyte or a keratinocyte.

Depending on the degree of commitment of a stem cell to a particular cell lineage, the present methods may also be used to direct stem cells to differentiate to phenotypically and functionally resemble a related but different cell type from the support cell, for example if prior to performing the present methods the stem cell is already committed to differentiating into a particular cell lineage that is different from the lineage of the support cells that provide the conditioned medium and ECM.

Alternatively, if the stem cells are to be proliferated in an undifferentiated state, the support cells chosen are cells that provide conditioned medium and ECM that maintain the stem cells in an undifferentiated state. For example, the support cells used may be MEFs, endometrial cells, or breast parenchymal cells.

The term "stem cell" refers to an undifferentiated cell that is capable of indefinite cell renewal and differentiation into a variety of cell types or a precursor cell that is partially differentiated along a particular cell lineage and for which further differentiation is restricted to cells of that particular lineage. "Stem cell" as used herein refers to any stem cell. The stem cell may be an embryonic stem cell or an adult stem cell, including for example a mesenchymal stem cell. The stem cell may be from any animal, including a mammal, including a human.

Methods of obtaining stem cells are known in the art. For example, undifferentiated hES cells are typically originally obtained from a blastocyst, as is known in the art, but may be previously expanded while kept in an undifferentiated state using known methods (22, 23). Mesenchymal stem cells may be obtained from bone marrow, peripheral blood, skin, hair roots, muscle tissues, endometrium and blood for example or from culture products of various tissues in which undifferentiated mesenchymal stem cells are expanded, as is known in the art (29, 31).

In order to culture the stem cell, the stem cell is grown in a stem cell culture medium that contains conditioned medium obtained from the culturing of the support cells.

The stem cell culture medium comprises any acceptable medium used to grow stem cells, including a basal growth medium or an enriched and/or supplemented growth medium, and including for example mesenchymal stem cell growth medium (MSGCM), Dulbecco's modified Eagle's medium (DMEM), knock-out DMEM or DMEM/F12 medium. If the stem cell is to differentiate into a particular type of cell, then the medium will be suitable for supporting the growth of the differentiated cell type, for example renal epithelial growth medium (REGM), renal epithelial basal medium (REBM), or RPMI-1640 medium.

The stem cell culture is supplemented with medium conditioned by a culture of the support cells. "Conditioned medium" or "medium conditioned by" refers to medium in which particular cells, in this case the support cells, have been cultured, releasing secreted factors such as growth factors or other cellular factors into the medium. It will be appreciated that the specific culture of support cells used to condition the medium does not need to be the culture used to extract the ECM; the support cells used for conditioning the medium should be of the same cell type and from the same species of organism as the support cells used as the source of the ECM. The conditioned medium may be obtained by growing the support cells in the medium for a single passage, for example for about 18 to about 24 hours, and then removing the medium from the support cells, including for example by pipetting and then centrifugation or filtration to remove remaining support cells.

The stem cell culture medium may comprise from about 20% (v/v) to about 70% (v/v), from about 30% (v/v) to about 60% (v/v), or from about 45% (v/v) to about (v/v) medium conditioned by the support cells. In a particular embodiment, the stem cell culture medium comprises about 50% (v/v) medium conditioned by the support cells.

The growth substrate used to culture the stem cell is ECM extracted from the support cells. The ECM is extracted from support cells using methods of decellularization that leave the ECM intact and able to adhere to the surface of the cell culture vessel in which the support cells are lysed. Generally, the support cells are collected and then lysed by applying a lysing reagent, for example water, an ammonia solution or detergent solution. Protease inhibitors may be included. After lysis, the cell culture vessel may be rinsed with PBS to remove residual lysis reagents and cellular debris that may detrimentally affect the stem cell culture.

For example, support cells may be lysed in a culture plate using 0.02 M ammonium hydroxide, the culture plate may be rinsed twice with PBS and the ECM on the culture plate can then be used as the growth substrate on which to culture the stem cell. It will be understood by those skilled in the art that a culture plate refers to any vessel in which cells can be cultured in vitro including for example plates, flasks or multi-welled plates.

Thus, the stem cell is cultured in a vessel that has been coated on an interior surface with the ECM extracted from the support cells, using stem cell culture medium that contains medium conditioned by the support cells.

As will be appreciated, culturing includes subjecting the stem cell to appropriate conditions to support the proliferation and optional differentiation of the stem cell, including cell passage, time, temperature, aeration, atmosphere and humidity.

When the present methods are performed to differentiate a stem cell population such as a cell culture, not every stem cell within the population or culture will necessarily differentiate. Thus, in the present method some stem cells within the population or culture may not differentiate and may retain their stem cell nature while other cells within the same population or culture are induced to differentiate and display the phenotype and functionality of the cells from which the ECM was extracted. For example, about 30% or greater, or about 35% or greater, or about 30% to about 45%, or about 35% to about 40% of the cells in the differentiated culture may have differentiated or may resemble or be comparable to the support cells used. For example, the present method may be used to induce differentiation of a population of hMS cells or a population of hES cells by seeding on ECM extracted from pancreatic insulin-secreting cells, such that the percentage of cells in the population that differentiate into cells that resemble pancreatic insulin-secreting cells is about 30% or greater, or about 35% or greater, or about 35% to about 40%, or about 36% or about 38%.

The extent of differentiation to cells of the desired cell type may be readily determined by a skilled person using standard methodology, including as described in the Examples below, such as immunostaining, PCR techniques to confirm expression of particular marker proteins and FACS analysis using an appropriate antibody.

Conveniently, the ECM used in the described methods is extracted from support cells that can be readily grown in culture, and thus the use of expensive purified or recombinant ECM molecules is not required. The use of an ECM extracted directly from support cells together with conditioned medium obtained from a culture of the support cells thus provides culture conditions containing the complete complement of ECM molecules that are found in the ECM of that cell, along with secreted factors produced by the support cells. These factors allow for quick, efficient proliferation and optional differentiation of the cultured stem cells.

Without being limited to any particular theory, it appears that by extracting the ECM directly from a support cell, the stem cell culture is provided with the same diversity of biological signals and effects supplied by the ECM when associated with the cell. For example, a stem cell cultured, in the absence of MEFs, on an ECM extracted from MEFs will undergo undifferentiated proliferation similar to the proliferation facilitated by MEFs. Similarly, a stem cell cultured on an ECM extracted from human proximal cells is induced to differentiate into proximal tubule cells much as it would if recruited to a damaged kidney in vivo.

The present methods also permit undifferentiated proliferation in vitro in the absence of an MEF feeder cell layer. Thus the present methods provide a protocol that overcomes the problem of cross contamination of human stem cells by MEFs by facilitating the undifferentiated proliferation of stem cells without the use of a MEF feeder cell layer.

The differentiated cells produced in the present methods demonstrate functional properties comparable to the support cells from which the conditioned medium is collected and the ECM is extracted. In one embodiment, stem cells induced to differentiate by seeding on ECM extracted from human proximal tubule cells demonstrate the capability to transport water comparable to human proximal tubule cells. In addition, the differentiated cells are capable of forming tubules on MATRIGEL™, indicating potential to form kidney tubules in the presence of the appropriate ECM.

In another embodiment, stem cells induced to differentiate by seeding on ECM extracted from pancreatic insulin-secreting cells demonstrate insulin production and secretion of insulin upon glucose challenge. In secreting insulin, the differentiated cells are responsive to glucose levels as indicated by fluctuations in the amount of insulin secreted by the differentiated cells throughout a cyclic exposure to media of low and high glucose concentration.

In another embodiment, stem cells induced to differentiate by seeding on ECM extracted from osteoblasts demonstrate expression of osteocalcin indicative of osteoblast function.

The functionality of cells differentiated in the present methods may be determined using available techniques, depending on the particular differentiated cell type. For example, as indicated in the Examples below, these techniques include determining the capacity of the differentiated cells to transport water by assaying for fluorescence before and after exposure to a hypotonic solution, using a fluorescent marker such as calcein. Techniques to determine the capacity of the differentiated cells to produce insulin in response to glucose challenge include assaying for expression of insulin during exposure to high and low glucose concentration, using an insulin c-peptide antibody.

Maintenance of undifferentiated cells following proliferation may be readily determined by a skilled person using standard methodology, including as described in the Examples below, such as immunostaining with antibodies against the octamer-binding transcription factors 3 and 4 (Oct 3/4) which are produced by hES cells but are down-regulated upon differentiation (35).

The present methods conveniently provide in vitro generation of cells that phenotypically and functionally resemble differentiated cells of a desired cell type. Thus, the present methods may be used to provide a useful and relatively inexpensive cell source for various biological applications including applications in cell therapeutics, tissue engineering, artificial organs, bihybrid implants, cell assays, drug screening and other research and development efforts.

It is known in the art that bioartificial devices can be used to perform organ functions in patients suffering from lost organ function (38-39). Bioartifical devices including biohybrid organs, are comprised of a combination of biological and artificial components (38). These devices can augment or replace organ function.

Due to their functionality, stem cells and differentiated cells produced according to the present methods provide a readily obtainable source of cells that may be used in bioartificial devices in strategies to replace lost organ function. Thus the present methods of culturing stem cells may be performed within a bioartificial device to provide differentiated cells that are functionally comparable to functioning cells of the organ sought to be treated by the bioartificial device. The method thus may comprise culturing stem cells in a bioartificial device in conditioned medium collected from and on ECM extracted from functioning cells of the organ sought to be treated by the device.

By performing the present methods of culturing stem cells within such a device, the resulting differentiated cells may be used in clinical applications while being separated by blood circulation via artificial immunological barriers, reducing risk of immune rejection or other immune complications and risk of possible tumourigenesis which may occur with undifferentiated stem cells.

In one example, the present methods may be used to culture stem cells within a bioartificial tubule assist device coated with ECM extracted from and in conditioned medium collected from human proximal tubule cells to provide differentiated cells that are functionally comparable to human proximal tubule cells. The bioartificial tubule assist device may then be used for the treatment of lost kidney function.

Cells cultured by the present methods may also be useful for treating a disorder in a subject, the disorder related to decreased cellular, tissue or organ function. A disorder relating to decreased cellular, tissue or organ function refers to a disorder in which cells, tissue or an organ of a subject has reduced or decreased function, impaired function, or are dysfunctional or non-functional compared to the cells, tissue or organ of an individual without the disorder.

Thus, stem cells cultured in conditioned medium collected from and on ECM extracted from cells of the cell type, tissue or organ affected in the disorder, and optionally differentiated into cells that are functionally comparable to cells of the cell type, tissue or organ affected in the disorder may be implanted in an effective amount into the subject where cells functionally comparable to said differentiated cells are required or into a bioartificial device used to treat the subject.

The cells or bioartificial device may be implanted using standard surgical or injection methods. The cells or device may be implanted at a suitable site in the subject to provide therapeutic treatment of the disorder related to lost cellular, tissue or organ function. Alternatively, the bioartificial device may be connected externally to the subject.

The term "effective amount" as used herein means an amount effective, at dosages and periods of time necessary to achieve the desired result, for example to treat the disorder related to lost cellular, tissue or organ function. The total number of cells to be administered will vary, depending on several factors, including the severity and type of the disorder, the mode of administration, and the age and health of the subject.

The subject may be any subject having a disorder related to lost cellular, tissue or organ function or requiring treatment for lost cellular, tissue or organ function.

For example, the cells produced by the present methods may be used to treat a subject with a renal related disorder. It is known that bioartificial tubule assist devices containing proximal tubule cells can provide renal reabsorption function to subjects with lost or impaired renal function (38, 39). The cells produced by the present methods may be used to treat a renal related disorder by providing subjects with differentiated cells that are functionally comparable to proximal tubule cells and that are provided in a bioartificial tubule assist device.

The cells produced by the present methods may also be used to treat disorders related to insulin deficiency. Diabetes mellitus (DM) is a disease that can be caused by an absolute insulin deficiency due to the destruction of insulin secreting pancreatic cells (Type 1) or by a relative insulin deficiency due to a combination of decreased insulin sensitivity and impaired function of insulin secreting cells (Type 2) (20, 41). A potential treatment for DM is the restoration of sufficient insulin production through transplantation of insulin secreting cells (41). Thus the cells produced by the present methods may treat an insulin deficiency disorder such as DM by providing subjects with differentiated cells that are functionally comparable to pancreatic insulin-secreting cells. Furthermore, the differentiated cells produced by the present methods may be used in bioreactors, as part of a bioartificial device such as a bioartificial pancreas or insulin producing device, to treat disorders related to insulin deficiency.

It will be appreciated that the cells produced by the present methods when administered for treatment of disorders related to lost cellular, tissue or organ function may be administered in combination with other treatments or therapies, including drug therapy and surgery.

"Treating" a disorder related to lost cellular, tissue or organ function refers to an approach for obtaining beneficial or desired results, including clinical results. Beneficial or desired clinical results can include, but are not limited to, alleviation or amelioration of one or more symptoms or conditions, diminishment of extent of disorder or disease, stabilization of the state of disease, prevention of development of disorder or disease, prevention of spread of disorder or disease, delay or slowing of disorder or disease progression, delay or slowing of disorder or disease onset, amelioration or palliation of the disorder or disease state, and remission (whether partial or total). "Treating" can also mean prolonging survival of a subject beyond that expected in the absence of treatment. "Treating" can also mean inhibiting the progression of disorder or disease, slowing the progression of disorder or disease temporarily, although more preferably, it involves halting the progression of the disorder or disease permanently.

The present methods are further exemplified by way of the following non-limited examples.

EXAMPLES

Materials and Methods
Cell Culture

Bone marrow mesenchymal stem cells: Bone marrow mesenchymal stem cells were commercially obtained from Lonza Inc. (Cat. #PT-2501), and cultured in mesenchymal stem cell growth medium (MSCGM, Cat. #PT3001).

MEF cells and hES cells (hESCs): HUES-7 cell line (obtained from Howard Hughes Medical Institute, USA) was cultured at 37° C. with 5% $CO_2$ on neomycin-resistant primary mouse fibroblasts (Cat. #PMEF-N, CHEMICON International, USA) in Knock-out Dulbecco's modified Eagle's medium (DMEM) (Cat. #10829018, Invitrogen, USA) and supplemented with 20% serum replacement (Cat. #10828028, Invitrogen, USA), 1% Glutamax (Cat. #35050061, Invitrogen, USA), 1% non-essential amino acid solution (Cat. #11140-050, Invitrogen, USA), 1% penicillin-streptomycin (Cat. #15070063, Invitrogen, USA), 10 ng/ml of bovine fibroblast growth factor (bFGF, Cat. #13526029, Invitrogen, USA) and 0.1% 2-beta mercaptoethanol (Cat. #21985023, Invitrogen, USA). The primary mouse fibroblasts (MEFs) were plated on a T75 flask coated with 0.1% gelatin (Sigma, USA). The culture medium was changed every day, and cultured for 7-10 days. The conditioned culture medium from MEFs was collected, and used for hESCs along with 10 ng/ml of bFGF. The hESCs cultured on the fibroblasts were trypsinized (0.05% Trypsin, Invitrogen, USA), scraped, and filtered through a 100-μm mesh. The filtered cells were cultured on a MATRIGEL™1 (BD Biosciences, Germany) coated (diluted 1:20 in Knock-out DMEM) culture flask containing conditioned medium from MEFs. Upon expansion, the cells were used in the differentiation protocol described below.

Human proximal tubule cells (HPTCs): Primary HPTCs were obtained commercially from Lonza (Cat #CC-2553), and cultured with renal epithelial growth medium (REGM, Cat #CC-3190, Lanza). The culture medium was changed every other day. The conditioned medium was collected, filtered, and used for the differentiation process.

Rat insulin-secreting cells (RIN5F): A cell line from rat pancreatic beta cell was obtained from ATCC (Cat #CRL-2058). The cells were cultured in RPMI-1640 medium containing 2 mM of L-glutamine, 1.5 g/L of sodium bicarbonate, 4.5 g/L of glucose, 10 mM of HEPES, 1.0 mM of sodium pyruvate, ITS supplement (insulin, transferrin and sodium selenium) and 10% of fetal bovine serum (PBS). The medium was changed every other day. The medium collected from RIN5F cells was filtered with 0.2-micron filter, and used as conditioned medium.

Mouse osteoblast cells: Mouse osteoblast cell line (MC3T3-E1) was obtained from ATCC (Cat #CRL-2594), and cultured in DMEM supplemented with 10% of PBS, 2 mM of L-glutamine and 1 mM of sodium pyruvate. The medium was changed every other day, and collected as conditioned medium.

RNA Isolation and Two-Step RT-PCR.

The total RNA was isolated from the cells using GeneElute total RNA isolation kit from Sigma (Cat. #RTN70) according to the manufacturer's protocol. The total RNA was cleared of any genomic DNA contamination by incubating with Rnase free Dnase I enzyme. The RNA was further reverse transcribed into cDNA using Superscript III reverse transcriptase enzyme (Invitrogen, USA). The specific gene of interest was amplified by PCR using advantage 2 polymerase enzyme (BD Biosciences, USA).

Differentiation Protocol

ECM was extracted from cultured committed cells, including HPTCs, rat insulin-secreting cells and mouse osteoblasts, by lysing with 0.02 ammonium hydroxide. After complete lysis, culture plates were washed twice with PBS, and stem cells were seeded onto the ECM laid by the committed cells. The cells were allowed to differentiate for at least 5-7 days in the presence of conditioned media.

Immunostaining and Flow Cytometry

Immunostaining: For immunostaining, 50% of confluent cells were grown on cover slips and fixed with paraformaldehyde. Fixed cells were incubated with appropriate primary antibody in the presence of 5% bovine serum albumin (BSA) at 4° C. overnight. Upon washing with phosphate-buffered saline (PBS) containing 1% of Triton X-100, the cells were incubated with complementary secondary antibody (fluorescent-labeled) for 2 h. The cover slips were then mounted and observed under laser confocal microscope.

Flow cytometry: About 1 million cells were suspended in 1 ml of ice-cold PBS containing 10% of PBS. Primary antibodies labelled with either fluorescein isothiocyanate (FITC) or rhodamine was added, and the cells were incubated for 30 min at 4° C. The cells were washed 3 times at 400 g for 5 min with ice-cold PBS containing 10% of PBS. The cells were resuspended in 1 ml of ice-cold PBS containing 10% of PBS. The sample was analyzed with a LSR IT 3-Laser FACS Analyzer (BD Biosciences, USA).

Functional Assays

Water transport assay using calcein: Cells were cultured in a monolayer on tissue culture plates at least 24 h prior to the assay. The cells were washed with PBS (without calcium and magnesium salts) 3 times for 1 min each. The cells were loaded with calceinAM (Invitrogen, USA) (1.6 μM final) in PBS for 10 min. They were washed with PBS 3 times for 1 min each. The cells were imaged under a fluorescent microscope with CCD camera. The medium was changed to a hypotonic solution (0.06% of NaCl in water). Time-lapse images were taken at an interval of 10 sec for 10 ruin. Metamorph software (Molecular Devices Co., CA, USA) was used to measure the fluorescence intensity.

c-Peptide assay for insulin measurement: Glucose-dependent insulin assay was used to check the functional potency of the differentiated cells. The assay was performed on the basic principle of sandwich ELISA. The c-peptide ELISA kit was obtained from Alpha Diagnostics (Cat. #040). The medium was collected and analyzed for the c-peptide secretion. For the cyclic induction of insulin secretion, the cells were exposed to a high glucose concentration (20 mM) for 1 h, followed by an exposure to a low glucose concentration (5 mM) for 1 h.

Undifferentiated Proliferation of hES Cells S

ECM was extracted from cultured MEFs by lysing with 0.02 ammonium hydroxide. After complete lysis, culture plates were washed twice with PBS. hES cells grown on a MEF feeder layer were trypsinized and seeded onto the ECM laid by the MEFs. The hES cells were cultured for 10-15 days and then subcultured onto ECM laid by MEFs. The hES cells were allowed to proliferate for at least 5-7 days in the presence of conditioned media.

Results

Figure 2:
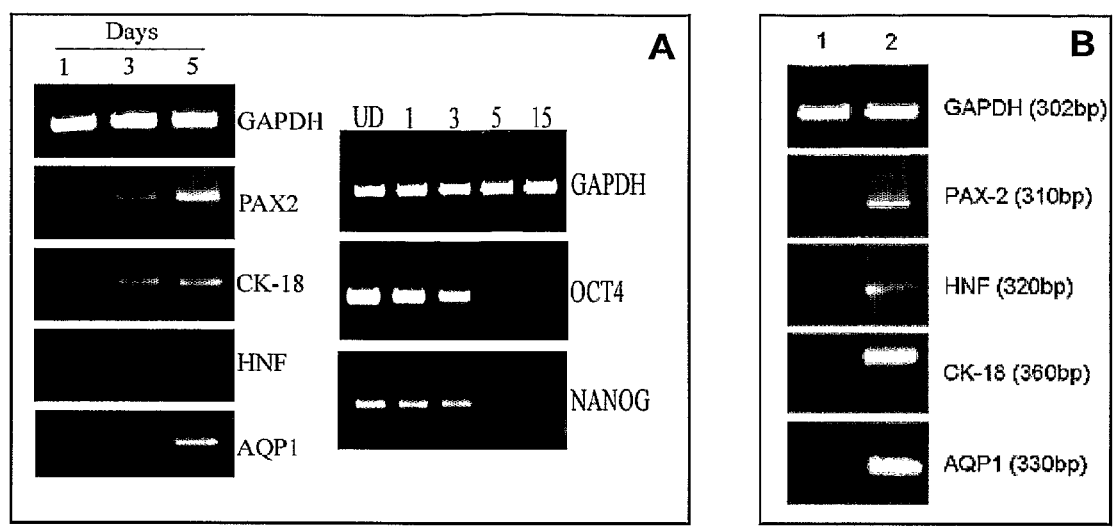
FIG. 2. Gene expression analysis of hES cells (hESCs) differentiated on ECM of HPTC. (A) RNA extracted from differentiated hESCs after the specified days of culture was tested by RT-PCR (reverse transcription PCR) for the expression of proximal tubule specific genes and stem cell specific marker genes. UD represents undifferentiated hESCs; 1, 3, 5 and 15 represent the days of differentiation. (B) Proximal tubule specific gene expression pattern of (1) undifferentiated hESCs, and (2) differentiated hESCs that have been subcultured 5 times on tissue culture dishes.
Figure 3:
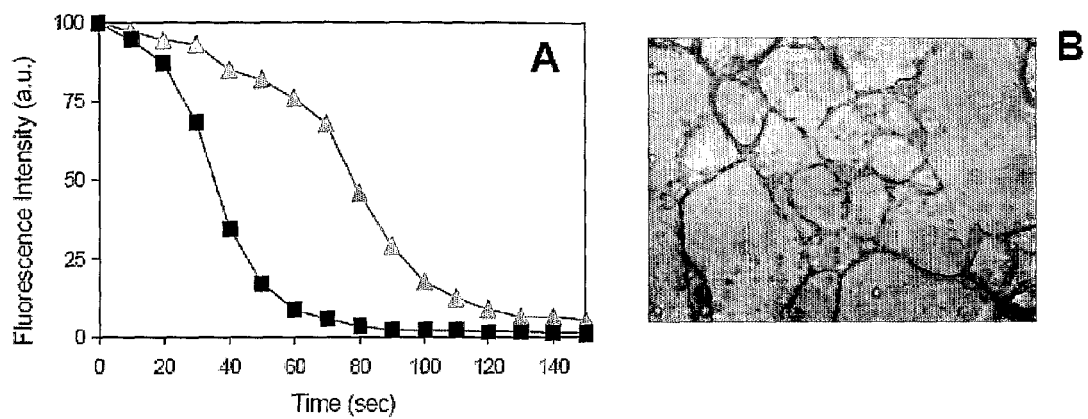
FIG. 3. Functional assays for hES cells differentiated on ECM of HPTC. (A) Water transport assay: fluorescence intensity of differentiated hESCs (▲; upper curve) and HPTCs (■; lower curve) (positive control) as a function of time. Calcein-loaded cells were exposed to hypotonic solution (30 mOsm) and the loss of fluorescence intensity was measured with a CCD camera and Metamorph software. (B) Tubule formation assay: cells were seeded on MATRIGEL™-coated dishes, and allowed to grow for 5 days. The differentiated cells were shown to form tubular structures.
Figure 4:
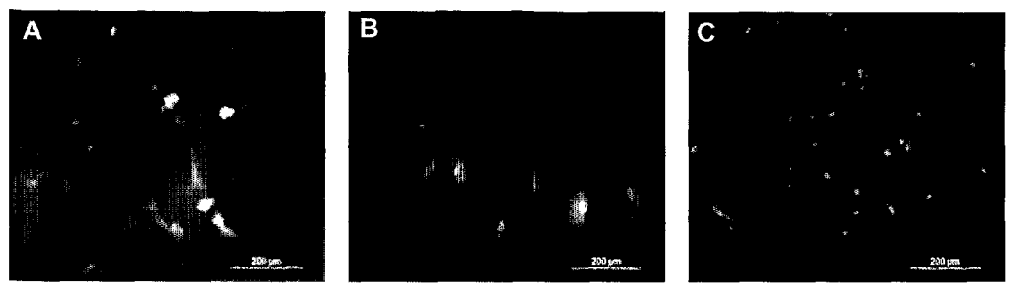
FIG. 4. Immunostaining of hESC differentiated on ECM of HPTC. Cells were fixed with paraformaldehyde and stained with (A) anti-Megalin antibody (B) anti-AQP1 antibody and (C) anti-PAX2 antibody.

Differentiation of hESCs into proximal tubule cells: The ECM of human proximal tubule cells (Lonza, Inc.) was used in the differentiation of hESCs into proximal tubule cells. The cells were cultured in the renal epithelial basal medium (REBM) at 1:1 ratio with filtered conditioned medium. The cells were allowed to differentiate for 10 days, and the medium was replenished every other day. The progress in differentiation was observed under light microscope (FIG. 1), and monitored by gene expression analysis (FIGS. 2A and 2B). Various markers for the differentiated proximal tubule cells increased progressively during the differentiation period, while the stem cell markers (Oct3/4 and Nanog) decreased gradually in expression. Specific genes such as Pax2 and AQP1 were expressed in the differentiated hESCs, indicating the proximal tubule phenotype of these cells. Functional assays were performed to test the functionality of these differentiated proximal tubule cells. A water transport assay was performed to demonstrate that these cells have the potential to transport water from inside to outside with the help of AQP1 protein. When the calcein-loaded cells were exposed to a hypotonic solution, the surge in osmotic water into the cells transported the calcein back to the outside of the cells. The cells lost their fluorescence intensity during this process. Therefore, calcein intensity was indirectly proportional to the water transport efficiency. The intensity at various time points was plotted in FIG. 3A. Human proximal tubule cells, which served as a positive control, took ~45-50 sec to lose 50% of the calcein intensity. In comparison, the differentiated hESCs required ~95-100 sec to loose 50% of the calcein intensity (FIG. 3A). Tubule formation on MATRIGEL™ (FIG. 3B) was also an indication that the differentiated hESCs have the potential to form kidney tubules in the presence of the appropriate ECM. Immunostaining with specific antibodies such as Megalin (FIG. 4A), AQP1 (FIG. 4B) and Pax2 (FIG. 4C) showed positive staining, indicating that the differentiated cells expressed these proteins.

Figure 5:
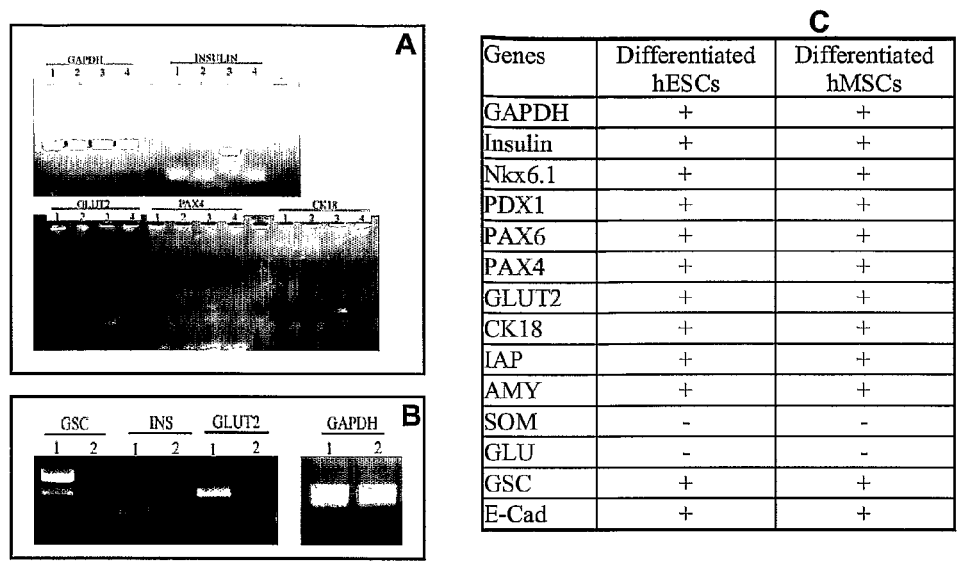
FIG. 5. Gene expression analysis of stem cells differentiated on ECM of insulin-producing cells. (A) RNA extracted from differentiated hMS cells (hMSCs) for analysis by RT-PCR of the expression of beta cell specific genes. (1) No serum, with ECM, (2) 10% of serum with ECM, (3) 10% of serum with ECM and conditioned media (1:1), and (4) co-culture with RINSF. (B) RNA extracted from (1) differentiated and (2) undifferentiated hESCs for analysis of the expression of beta cell specific genes. (C) Table indicating the positive expression of various genes involved in the beta cell phenotype development. Highlighted are marker genes specific for the pancreatic beta cell.
Figure 6:
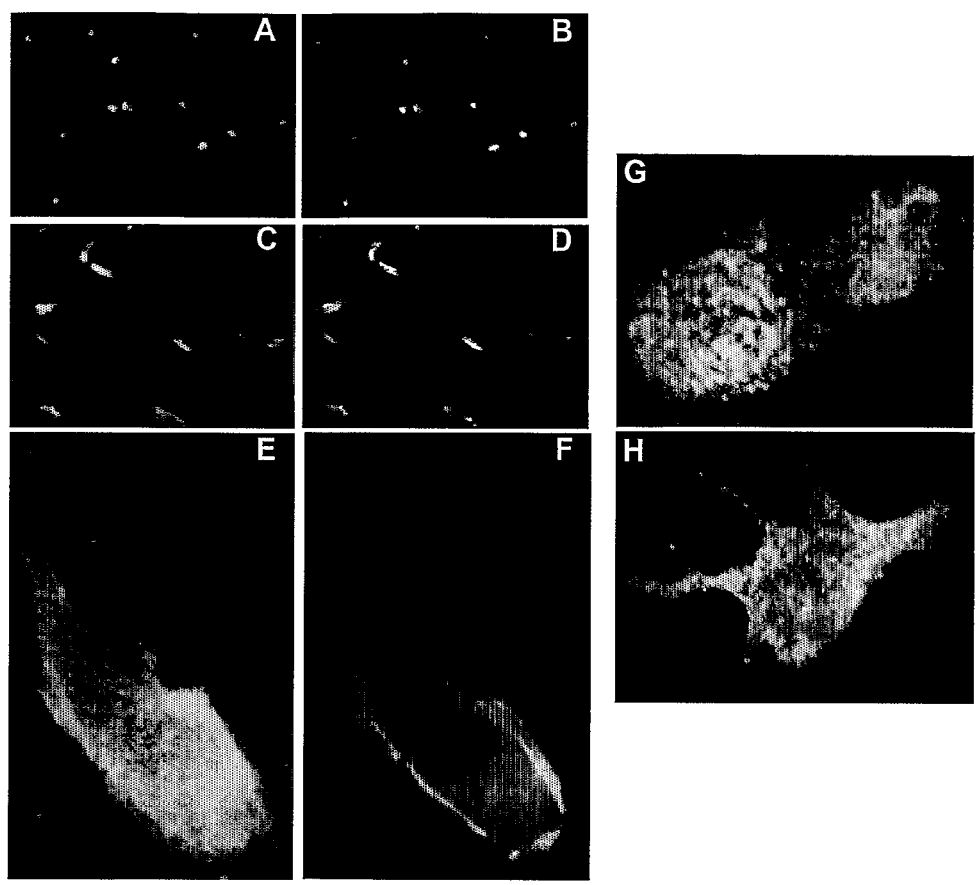
FIG. 6. Immunostaining of stem cells differentiated on ECM of insulin-producing cells. The differentiated hESCs (A, B, G) and hMSCs (C-F, H) were fixed with paraformaldehyde and immunostained with anti-PDX1 (A, C), anti-human insulin C-peptide (B, D, E, G, H), and anti-Glut2 (F) antibodies. Images were obtained with laser confocal microscopy.
Figure 7:
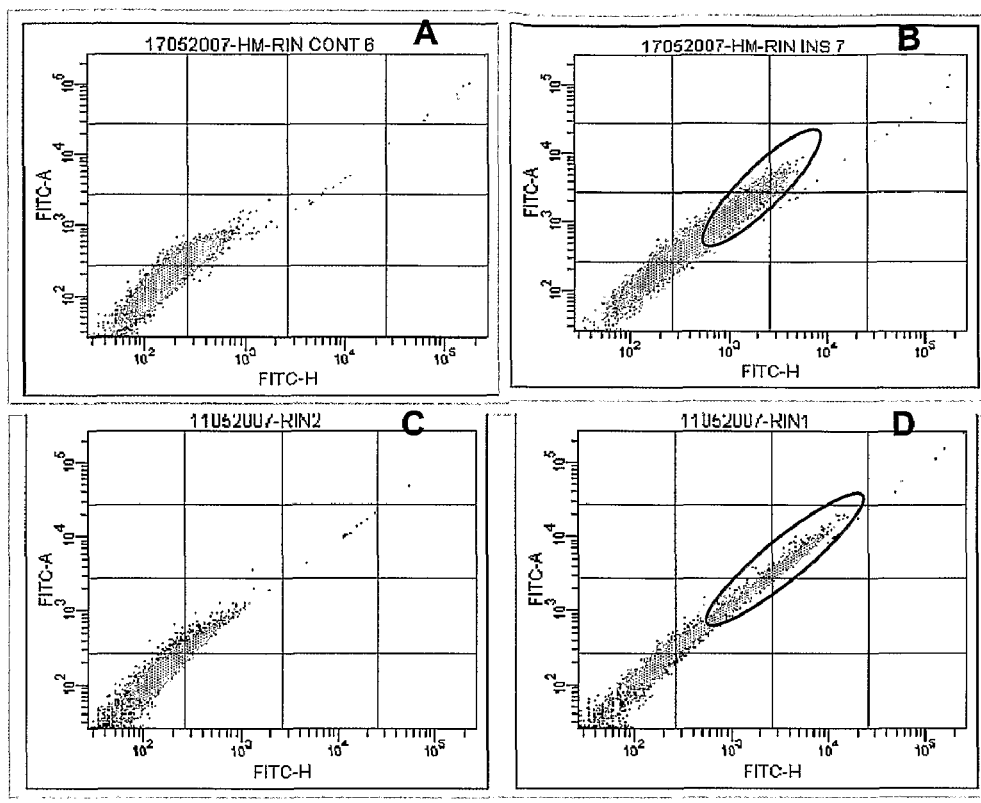
FIG. 7. Flow cytometry analysis of the insulin-secreting cells. The differentiated hMSCs (B) and hESCs (D) were analyzed with human c-peptide antibody using LSR II 3laser FACS analyzer, along with the isotype control hMSCs (A) and hESCs (C).
Figure 8:
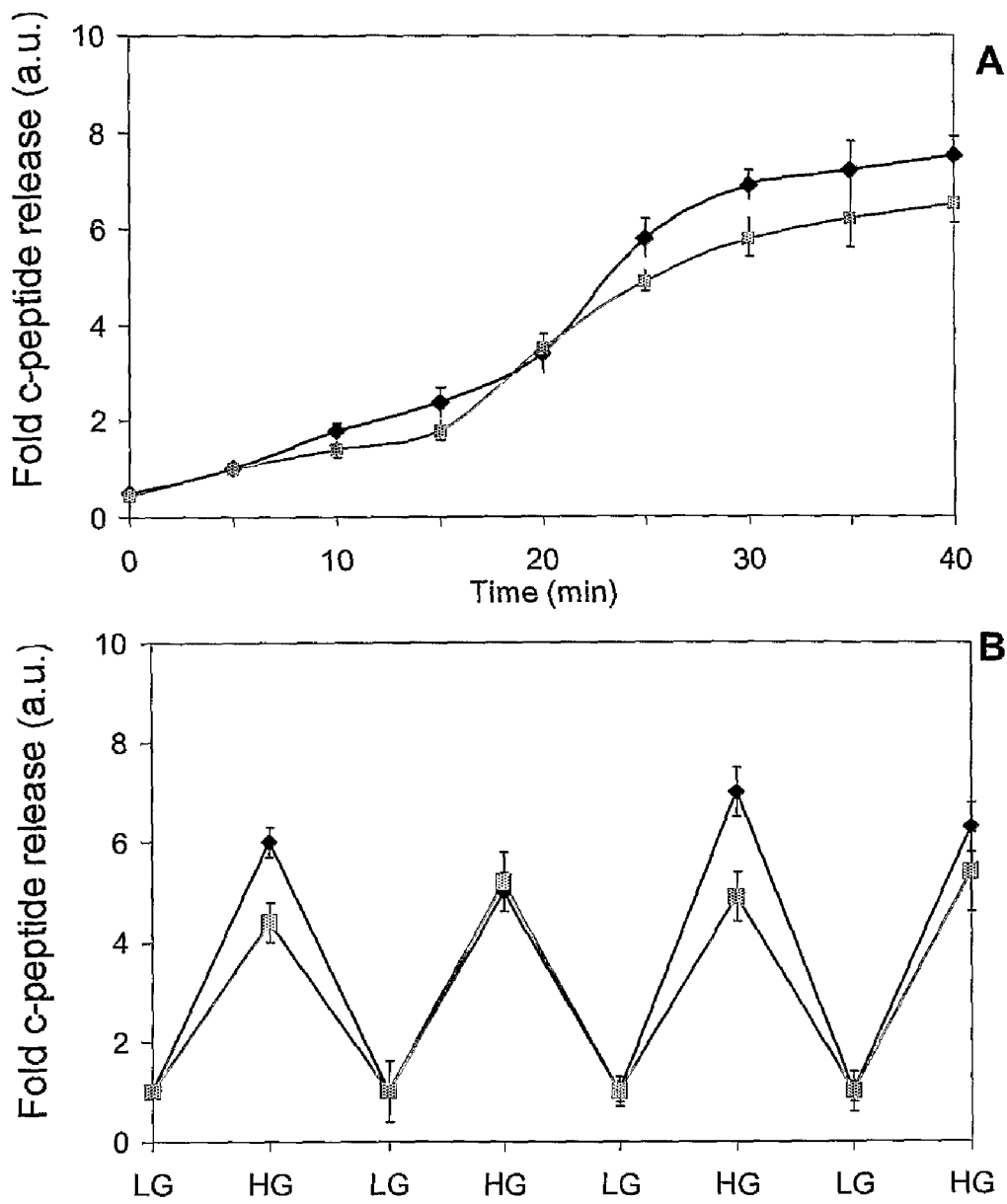
FIG. 8. Functional assays for stem cells differentiated on ECM of insulin-producing cells. The release of c-peptide as a function of insulin production was measured using c-peptide ELISA for the differentiated (♦) hESCs and (■) hMSCs. (A) The secretion of c-peptide in response to high glucose concentration (20 mM) was assayed over a period of time. (B) Cyclic response of c-peptide secretion to media of low glucose concentration (LH=5 mM) and high glucose concentration (HG=20 mM).

Differentiation of hESCs and hMS cells (hMSCs) into insulin-producing cells: The ECM from the rat insulin-producing cells (RIN5F) was used for the differentiation of stem cells. hESCs and hMSCs were seeded onto the ECM, and differentiated into insulin producing cells with typical beta cell phenotype. Gene expression analysis indicated that the presence of serum (10%) and ECM triggered the differentiation of the stem cells. The expression of insulin, Pax4, Glut2 and CK18 were detected when the stem cells were allowed to differentiate in the presence of serum and ECM (FIGS. 5A and B). The list of genes that were positively detected is shown in FIG. 5C. Immunostaining with specific antibodies showed positive staining for the differentiated cells (FIG. 6). Human insulin c-peptide antibody also detected positive cells. Higher magnification images revealed a typical secretory granular staining for the c-peptide antibody (FIGS. 6G and H). Further staining with Glut2 antibody showed typical plasma membrane localization (FIG. 6F). In order to identify the ratio of the insulin-producing cells in the differentiated pool of cells, FACS was performed with c-peptide antibody. FACS analysis indicated that ~36% and 38% of positive cells were attained for the differentiated hMSCs and hESCs, respectively (FIG. 7). These differentiated cells were analyzed for their responsiveness towards insulin secretion upon glucose challenge. Saturation of c-peptide secretion was observed after 60 min of exposure to a medium of high glucose concentration (20 mM), which remained saturated at later time points (FIG. 8A). We also observed that the differentiated cells responded to cyclic exposure of media of low and high glucose concentrations. The responsiveness was maintained for at least 3 cycles (FIG. 8B).

Figure 9:
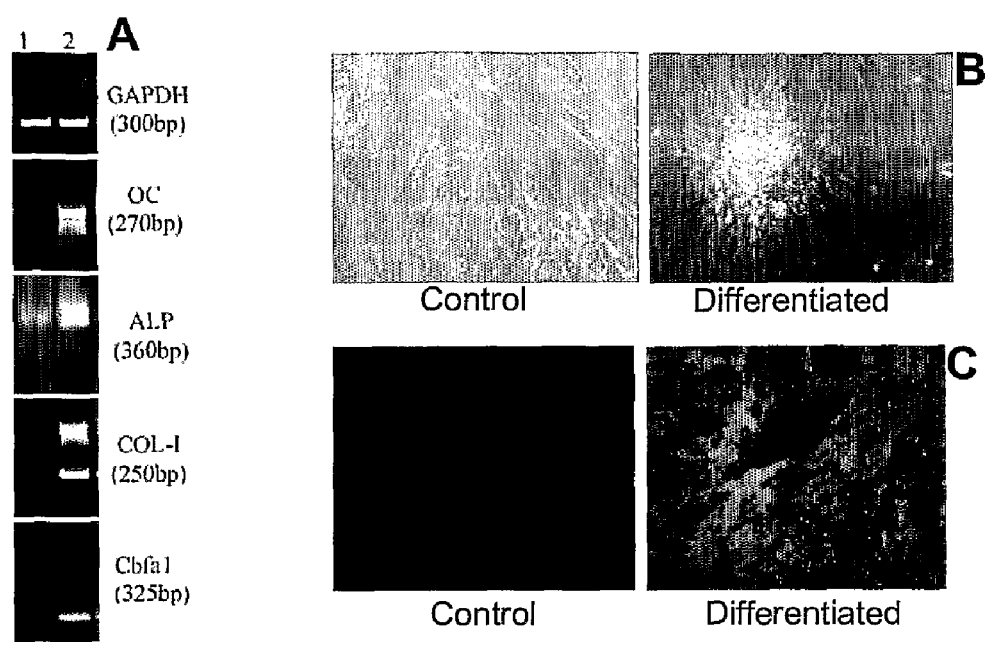
FIG. 9. Differentiation of hMS cells into osteoblasts. (A) Gene expression analysis by RT-PCR. Osteocalcin (OC), alkaline phosphatase (ALP), type I collagen (COL-I) and cbfa1 genes were analyzed using the specific primers. Lane 1 represents the undifferentiated hMS cells and lane 2 represents the differentiated hMSC. (B) Light microscopy images of undifferentiated and differentiated hMSCs on day 12 after induction of differentiation. (C) Immunostaining showing positive expression of osteocalcin in the differentiated hMSCs.
Figure 10:
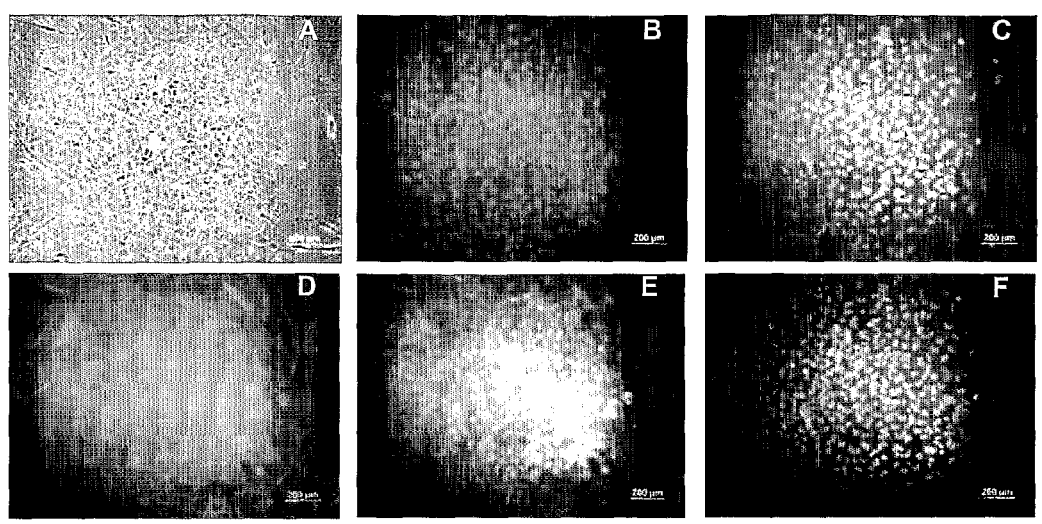
FIG. 10. Proliferation of hESCs grown on ECM isolated from MEFs. (A) Light microscopy image. (B) Immunostaining with monoclonal Oct3/4 antibody. (C) Nuclear staining by DAPI. (D) Tubulin staining by Phalloidin-FITC. (E) Composite of B and D. (F) Composite of B and C.

Differentiation of hMSCs into osteoblasts: ECM isolated from osteoblasts was used to differentiate the hMSCs into an osteoblast phenotype. Successful differentiation of hMSCs into osteoblasts was confirmed by gene expression analysis and immunostaining with osteocalcin antibody. RT-PCR analysis showed the expression of osteoblast-specific marker genes such as type I collagen, osteocalcin, and Cbfa1 (FIG. 9A). Immunostaining with osteocalcin antibody showed positive staining, indicating the expression of osteocalcin (FIG. 9C). Differentiated and undifferentiated cells were also viewed using light microscopy (FIG. 9B).

hESCs cultured on MEF's ECM: In an attempt to simplify the embryonic stem cell culture, MEF's ECM was used as a substrate for the culture of hESCs. hESCs were seeded onto the MEF's ECM, and cultured for 10-15 days. The cells were subcultured onto MEF's ECM. Upon 2 passages on MEF's ECM, the cells were stained with stem cell marker antibody (Oct3/4). Immunostaining with Oct3/4 showed the positive expression in hESC colonies (FIG. 10).

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Concentrations given in this specification, when given in terms of percentages, include weight/weight (w/w), weight/volume (w/v) and volume/volume (v/v) percentages.

As used in this specification and the appended claims, the singular forms "a", "an" and "the" include plural reference unless the context clearly dictates otherwise. As used in this specification and the appended claims, the terms "comprise", "comprising", "comprises" and other forms of these terms are intended in the non-limiting inclusive sense, that is, to include particular recited elements or components without excluding any other element or component. Unless defined otherwise all technical and scientific terms used herein have the same meaning as commonly understood to one of ordinary skill in the art to which this invention belongs.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

References

1. Singec, I; Jandial, R; Crain, A; Nikkhah, G; Snyder, E Y (2007) The leading edge of stem cell therapeutics. *Annual Reviews in Medicine* 58: 313-328.
2. Findikli, N; Candan, N Z; Kahraman, S (2006) Human embryonic stem cell culture: Current limitations and novel strategies. *Reproductive Biomedicine Online* 13: 581-590.
3. Wobus, A M; Boheler, K R (2005) Embryonic stem cells: Prospects for developmental biology and cell therapy. *Physiological Reviews* 85: 635-678.
4. Barry, FP; Murphy, J M (2004) Mesenchymal stem cells: Clinical applications and biological characterization. *International Journal of Biochem. and Cell Biol.* 36: 568-584.
5. Filipczyk, A A; et al. (2007) Regulation of cardiomyocyte differentiation of embryonic stem cells by extracellular signaling. *Cell. and Mol Life Sciences* 64: 704-718.
6. van Wijk, B; Moorman, A F M; van den Hoff, M J B (2007) Role of bone morphogenetic proteins in cardiac differentiation. *Cardiovascular Research* 74: 244-255.
7. Ye, P; D'Ercole, A J (2006) Insulin-like growth factor actions during development of neural stem cells and progenitors in the central nervous system. *J Neuroscience Research* 83: 1-6.
8. Spagnoli, F M; Hemmati-Brivanlou, A (2006) Guiding embryonic stem cells towards differentiation: Lessons from molecular embryology. *Current Opinion in Genetics and Development* 16: 469-475.
9. Berry, M F; et al. (2006) Mesenchymal stem cell injection after myocardial infarction improves myocardial compliance. *Am J Physiology Heart and Circulatory Physiology* 290: H2196-H2203.
10. Murry, C E; Reinecke, H; Pabon, L M (2006) Regeneration gaps—Observations on stem cells and cardiac repair. *J American College of Cardiology* 47: 1777-1785.
11. Lange, C; et al. (2005) Administered mesenchymal stem cells enhance recovery from ischemia/reperfusion-induced acute renal failure in rats. *Kidney International* 68: 1613-1617.
12. Kajstura, J; et al. (2005) Bone marrow cells differentiate in cardiac cell lineages after infarction independently of cell fusion. *Circulation Research* 96: 127-137.
13. Chen, S L; et al. (2004) Effect on left ventricular function of intracoronary transplantation of autologous bone marrow mesenchymal stem cell in patients with acute myocardial infarction. *Am J Cardiology* 94: 92-95.
14. Nakano, K; et al. (2001) Differentiation of transplanted bone marrow cells in the adult mouse brain. *Transplantation* 71: 1735-1740.
15. Kopen, G C; Prockop, D J; Phinney, D G (1999) Marrow stromal cells migrate throughout forebrain and cerebellum, and they differentiate into astrocytes after injection into neonatal mouse brains. *PNAS* 96: 10711-10716.
16. Pluchino, S; et al. (2003) Injection of adult neurospheres induces recovery in a chronic model of multiple sclerosis. *Nature* 422: 688-694.
17. Little, M. H. Regrow or repair: Potential regenerative therapies for the kidney. *J Am Soc Nephrol* 17, 2390-2401 (2006).
18. Wang, G. et al. Noggin and bFGF cooperate to maintain the pluripotency of human embryonic stem cells in the absence of feeder layers. *Biochem Biophys Res Commun* 330, 934-942 (2005).
19. Pittenger, M. et al. Multilineage potential of adult human mesenchymal stem cells. *Science.* 1999 Apr. 2; 284(5411):143-7.
20. Chen, L. Jiang, X. and Yang, L. Differentiation of rat marrow mesenchymal stem cells into pancreatic islet beta-cells. *World J Gastroenterol.* 2004 Oct. 15; 10(20):3016-20
21. Flaim C J, Chien S, Bhatia S N. An extracellular matrix microarray for probing cellular differentiation. *Nat Methods.* 2005 February; 2(2):119-25.
22. Amit, M and Itskovitz-Eldor, J. Feeder-free culture of human embryonic stem cells. *Methods Enzymol.* 2006; 420:37-49.
23. Chase L. and Firpo, M. Development of serum-free culture systems for human embryonic stem cells. *Curr Opin Chem Biol.* 2007 August; 11(4):367-72.
24. Ellerström C. et al. Derivation of a xeno-free human embryonic stem cell line. *Stem Cells.* 2006 October; 24(10):2170-6
25. Suzuki, A. et al. Role for growth factors and extracellular matrix in controlling differentiation of prospectively isolated hepatic stem cells. *Development.* 2003 June; 130(11):2513-24
26. Haylock D. and Nilsson, S. Stem cell regulation by the hematopoietic stem cell niche. *Cell Cycle.* 2005 October; 4(10):1353-5.
27. Kihara, T. et al. Exogenous type I collagen facilitates osteogenic differentiation and acts as a substrate for mineralization of rat marrow mesenchymal stem cells in vitro. *Biochem Biophys Res Commun.* 2006 Mar. 24; 341(4):1029-35.
28. Chen, S. et al. Cell-cell and cell-extracellular matrix interactions regulate embryonic stem cell differentiation. *Stem Cells.* 2007 March; 25(3):553-61.
29. Xu, C. et al. Feeder-free growth of undifferentiated human embryonic stem cells. *Nat Biotechnol.* 2001 October; 19(10):971-4.
30. Naugle, J. et al. Type VI collagen induces cardiac myofibroblast differentiation: implications for postinfarction remodeling. *Am J Physiol Heart Circ Physiol.* 2006 January; 290(1):H323-30.
31. European Patent Application EP 1669441 Method of differentiating mesenchymal stem cell into liver cell and artificial human liver cell.
32. PCT Patent Application WO 2007/117472 Adult bone marrow cell transplantation to testes creation of transdifferentiated testes germ cells, leydig cells and sertoli cells.
33. U.S. Patent Application US 2007/0155009 Extracellular matrix components for expansion or differentiation of hepatic progenitors.
34. Ludwig, T. et al. Derivation of human embryonic stem cells in defined conditions. *Nat Biotechnol.* 2006 February; 24(2):185-7.
35. Derda, R. et al. Defined substrates for human embryonic stem cell growth identified from surface arrays. *ACS Chem Biol.* 2007 May 22; 2(5):347-55.
36. Rajala, K. et al., Testing of nine different xeno-free culture media for human embryonic stem cell cultures. *Hum Reprod.* 2007 May; 22(5):1231-8.
37. Stojkovic, P. et al., Human-serum matrix supports undifferentiated growth of human embryonic stem cells. *Stem Cells.* 2005 August; 23(7):895-902.
38. Humes, H. D. et al. Initial clinical results of the bioartificial kidney containing human cells in ICU patients with acute renal failure. *Kidney Int* 66, 1578-1588 (2004).
39. Tiranathanagul, K., Brodie, J. & Humes, H. D. Bioartificial kidney in the treatment of acute renal failure associated with sepsis. *Nephrology (Carlton)* 11, 285-291 (2006).

40. D'Amour, K. et al. Production of pancreatic hormone-expressing endocrine cells from human embryonic stem cells. *Nat Biotechnol.* 2006 November; 24(11):1392-401.
41. Segev, H. et al. Differentiation of human embryonic stem cells into insulin-producing clusters. *Stem Cells.* 2004; 22(3):265-74.
42. Meyer, C. et al. Improved glucose counterregulation and autonomic symptoms after intraportal islet transplants alone in patients with long-standing type I diabetes mellitus. *Transplantation.* 1998 Jul. 27; 66(2):233-40.
43. Juang, J. et al. Outcome of subcutaneous islet transplantation improved by polymer device. *Transplantation.* 1996 Jun. 15; 61

What is claimed is:

1. A method of directing differentiation of a human stem cell into a pre-selected cell type, said method comprising culturing the human stem cell on extracellular matrix extracted from differentiated support cells and in a stem cell culture medium comprising from about 20% (v/v) to about 70% (v/v) medium conditioned by the differentiated support cells and free from the differentiated support cells, to promote differentiation of the stem cell into said pre-selected cell type, wherein (i) the human stem cell is a human embryonic stem cell, the pre-selected cell type is a proximal tubule cell, and the differentiated support cells are proximal tubule cells; (ii) the human stem cell is a human embryonic stem cell or a human mesenchymal stem cell, the pre-selected cell type is an insulin-producing cell, and the differentiated support cells are pancreatic insulin-secreting cells; or (iii) the human stem cell is a human mesenchymal stem cell, the pre-selected cell type is an osteoblast, and the differentiated support cells are osteoblasts, and wherein for (ii) the stem cell culture medium comprises 10% serum.

2. The method according to claim 1 wherein the human stem cell is a human embryonic stem cell, the pre-selected cell type is a proximal tubule cell and the differentiated support cells are human proximal tubule cells.

3. The method according to claim 1 wherein the human stem cell is a human embryonic stem cell or a human mesenchymal stem cell, the pre-selected cell type is an insulin-producing cell and the differentiated support cells are pancreatic insulin-secreting cells.

4. The method according to claim 1 wherein the human stem cell is a human mesenchymal stem cell, the pre-selected cell type is an osteoblast and the differentiated support cells are osteoblasts.

5. The method according to claim 1 wherein the human stem cell is a human embryonic stem cell.

6. The method according to claim 1 wherein the human stem cell is a human mesenchymal stem cell.

7. The method according to claim 1 wherein the human stem cell is cultured in a tissue culture plate or culture flask.

8. The method according to claim 1 wherein the human stem cell is cultured in a bioartificial device.

9. The method according to claim 8 wherein the bioartificial device is a bioartificial tubule assist device and the human stem cell is a human embryonic stem cell, the pre-selected cell type is a proximal tubule cell and the differentiated support cells are human proximal tubule cells.

10. The method according to claim 1 wherein the stem cell culture medium comprises about 45% (v/v) to about 55% (v/v) medium conditioned by the differentiated support cells.

* * * * *